United States Patent [19]

Kulprathipanja et al.

[11] Patent Number: 5,177,300
[45] Date of Patent: Jan. 5, 1993

[54] PROCESS FOR SEPARATING NAPHTHALENE FROM SUBSTITUTED BENZENE HYDROCARBONS

[75] Inventors: Santi Kulprathipanja, Inverness; Kenneth Kuhnle, St. Charles; Marjorie S. Patton, Darien; Richard L. Fergin, Mount Prospect, all of Ill.

[73] Assignee: UOP, Des Plaines, Ill.

[21] Appl. No.: 790,905

[22] Filed: Nov. 12, 1991

[51] Int. Cl.⁵ ............................................. C07C 7/13
[52] U.S. Cl. ............................... 585/828; 585/820; 585/826
[58] Field of Search ............ 585/820, 826, 828; 208/310 Z

[56] References Cited

U.S. PATENT DOCUMENTS

| | | |
|---|---|---|
| 2,985,589 | 5/1961 | Broughton et al. ............... 210/34 |
| 3,040,777 | 6/1962 | Carson et al. ................. 137/625.15 |
| 3,422,848 | 1/1969 | Liebman et al. ............... 137/625.15 |
| 3,697,414 | 10/1972 | Carpenter et al. .................... 208/85 |
| 3,706,812 | 12/1972 | De Rosset et al. ............ 260/674 SA |
| 4,357,276 | 11/1982 | Takasa et al. ..................... 260/319.1 |
| 4,642,397 | 2/1987 | Zinnen et al. ......................... 568/934 |
| 4,962,273 | 10/1990 | Zinnen et al. ......................... 585/831 |
| 4,992,621 | 2/1991 | Zinnen ................................. 585/826 |
| 5,107,062 | 4/1992 | Zinnen ................................. 585/828 |

Primary Examiner—Anthony McFarlane
Attorney, Agent, or Firm—Thomas K. McBride; John F. Spears, Jr.; Jack H. Hall

[57] ABSTRACT

The separation of naphthalene in high purity from coal tar or petroleum fractions by an adsorptive chromatographic process and liquid phase with lithium-exchanged X zeolite as the adsorbent and aromatic desorbents.

5 Claims, 1 Drawing Sheet

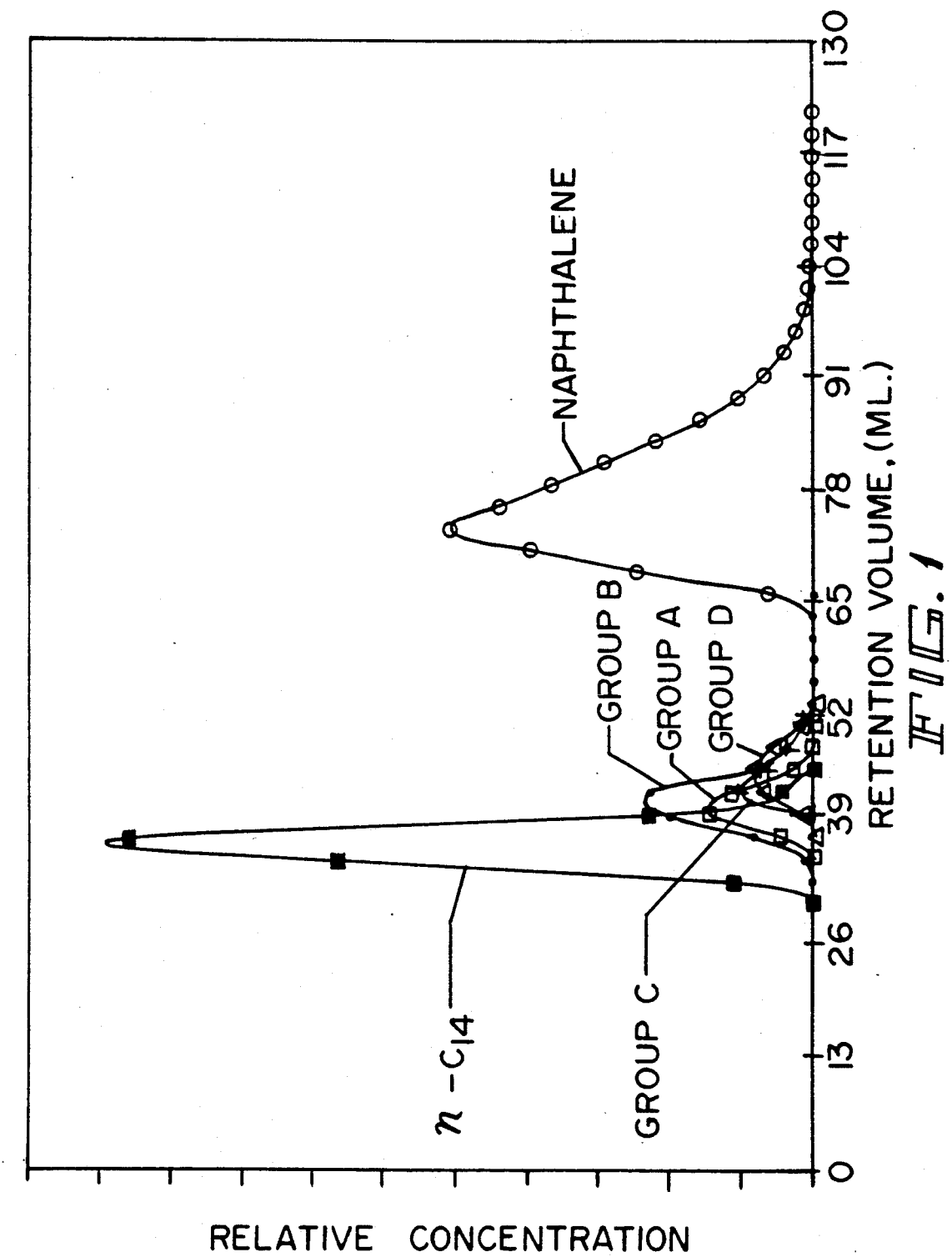

PROCESS FOR SEPARATING NAPHTHALENE FROM SUBSTITUTED BENZENE HYDROCARBONS

FIELD OF THE INVENTION

The field of art to which this invention belongs is the solid bed adsorptive separation of naphthalene. More specifically, the invention relates to a process for separating naphthalene from a coal tar distillate containing substituted benzene hydrocarbons boiling in the same range.

BACKGROUND OF THE INVENTION

Naphthalene in purified form is in substantial demand as an intermediate for a variety of uses, for example, synthetic resins, textile chemicals, tetralin, decalin, etc. Tetralin and decalin are useful as desorbents in chromatographic bulk separations. A readily available source of naphthalene is coal tar distillates or fractions resulting from catalytic processing of petroleum. Normally, purification is accomplished by crystallization and/or distillation of a fraction having a narrow boiling point range and/or melting point, but a large number of theoretical stages is required.

The separation of naphthalene from light cycle oils from catalytic cracking processes by adsorption with activated carbon has been disclosed in U.S. Pat. No. 3,697,414. Carbon adsorbents, however, generally have low capacities and adsorption-desorption rates. To overcome these drawbacks, an adsorbent with higher capacity and faster desorption rates is desired.

U.S. Pat. No. 4,357,276 discloses that indole may be separated from a coal tar fraction containing naphthalene and 2-methylnaphthalene, on X and Y type zeolites exchanged with Group IA cations whereby indole is selectively adsorbed by the zeolite and naphthalene is co-rejected with the other components of the coal tar fraction. Various desorbents are disclosed, but there is no suggestion that the adsorbent-desorbent combination of the invention is capable of selectively adsorbing naphthalene and rejecting other components in the naphthalene mixture.

Eremenko et al, Teor. Eksp. Khim., 5(2), pp 242–6 (1969), have disclosed that naphthalene could be adsorbed on Type X zeolite with a variety of dual metal exchange ions, e.g., LiNaX, etc., but no suggestion that naphthalene could be separated from a commercially-available feedstock or with LiX was made.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRosset U.S. Pat. No. 3,706,812) to commercial scale in flow rates from a few cc per hour to many thousands of gallons per hour.

The functions and properties of adsorbents and desorbents in the chromatographic separation of liquid components are well known, but for reference thereto, Zinnen et al U.S. Pat. No. 4,642,397 is incorporated herein.

We have found a specific adsorbent which, in combination with certain desorbent liquids, will selectively adsorb naphthalene from a coal tar distillate feedstock containing naphthalene, substituted monocyclic aromatic compounds (including dicyclic compounds, such as indan) and paraffins.

SUMMARY OF THE INVENTION

The present invention is a process for separating naphthalene from hydrocarbon mixture comprising naphthalene, monocyclic aromatic hydrocarbons and paraffins boiling in the range from 200° to 250° C., the steps comprising contacting the hydrocarbon mixture, under adsorption conditions, with an X zeolite adsorbent exchanged with lithium atoms at the exchangeable sites. Naphthalene is selectively adsorbed to the substantial exclusion of other components, thereby selectively adsorbing said naphthalene thereon. The other components, monocyclic aromatic hydrocarbons and paraffins, are removed from contact with the adsorbent and naphthalene is desorbed with a liquid aromatic desorbent having a boiling point at least 5° higher or lower than the boiling point range of said hydrocarbon mixture, for example, 1,2,3-trimethylbenzene (hemimellitene, sometimes 1,2,3-TMB herein) 1,3,5-trimethylbenzene (mesitylene), toluene, p-xylene, benzene and m-xylene. The preferred desorbents are 1,2,3-TMB and benzene.

Other embodiments of our invention encompass details about feed mixtures, adsorbents, desorbent materials and operating conditions, all of which are hereafter disclosed in the following discussion of the present invention.

BRIEF DESCRIPTION OF THE DRAWING

FIG. 1 comprises the chromatographic trace of the pulse test of Example I showing the separation of naphthalene from a coal tar distillate with lithium exchanged X zeolite adsorbent and 1,2,3-trimethylbenzene as desorbent.

DETAILED DESCRIPTION OF THE INVENTION

Adsorbents to be used in the process of this invention comprise specific crystalline aluminosilicates or molecular sieves, namely X zeolites, exchanged at exchangeable cationic sites with lithium ions. The zeolites have known cage structures in which the alumina and silica tetrahedra are intimately connected in an open three-dimensional network to form cage-like structures with window-like pores. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves", although widely used, is not strictly suitable since the separation of naphthalene from other aromatic hydrocarbons having similar boiling points is apparently dependent on differences in electrochemical attraction of the different isomers and the adsorbent rather than on pure physical size differences in the isomer molecules.

In hydrated or partially hydrated form the preferred type X crystalline aluminosilicates encompass those zeolites represented, in terms of moles of metal oxides, by the formula 1 below:

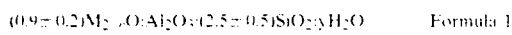

$$(0.9 \pm 0.2)M_{2/n}O:Al_2O_3:(2.5 \pm 0.5)SiO_2:yH_2O \qquad \text{Formula 1}$$

where "M" is a cation which balances the electrovalence of the tetrahedra and is generally referred to as an exchangeable cationic site. "n" represents the valence of the cation and "y" represents the moles of water.

Adsorbents comprising the type X zeolites are useful for the adsorptive process for extracting naphthalene from hydrocarbon mixtures herein described. These zeolites are described and defined in U.S. Pat. No. 2,882,244. The term "type X structured" zeolites as used herein shall include all zeolites which have general structures as represented in the above cited patent.

Typically, the type X structured zeolites, as initially prepared, are predominantly in the sodium form. The term "exchanged cationic site" generally refers to the site in the zeolite occupied by the cation "M". This cation, usually sodium, can be replaced or exchanged with other specific cations, dependent on the type of the zeolite to modify characteristics of the zeolite. The preferred zeolites for use in this invention are type X zeolites exchanged with lithium ions.

Cations occupying exchangeable cationic sites in the zeolite are exchanged with other cations by ion exchange methods well known to those having ordinary skill in the field of crystalline aluminosilicates. Such methods are generally performed by contacting the zeolite or an adsorbent material containing the zeolite with an aqueous solution of the soluble salt, e.g., the chloride of the cation or cations desired to be placed upon the zeolite. After the exchange takes place, the sieves are removed from the aqueous solution, washed, then dried to a desired water content. By such methods, the sodium cations and any non-sodium cations which might be occupying exchangeable sites as impurities in a sodium-X zeolite can be essentially completely replaced with lithium cations. Adsorbents preferred for this process have a particle size range of from about 20 to about 40 U.S. Mesh. The term "essentially complete" shall mean that the residual sodium content of the adsorbent after the ion exchange of the base material shall be less than about 2 wt. % $Na_2O$. The water content of the adsorbent as measured by loss on ignition (LOI) at 900° C. may be from about 0.5 to about 4 wt. %, and most preferably about 0.5 to 2.0 to wt. % (LOI). Water may be added to the adsorbent, if necessary, either on an intermittent or more preferably on a continuous basis, separately or in admixture with feed or desorbent material, to maintain the desired concentration of water on the adsorbent.

Typically, adsorbents used in separative processes contain the crystalline material dispersed in an amorphous inorganic matrix or binder, having channels and cavities therein which enable liquid access to the crystalline material. Amorphous material such as silica, or silica-alumina mixtures or compounds, such as clays, are typical of such inorganic matrix materials. The binder aids in forming or agglomerating the crystalline particles of the zeolite which otherwise would comprise a fine powder. The adsorbent may thus be in the form of particles such as extrudates, aggregates, tablets, macrospheres or granules having a desired particle size range, from about 16 to about 40 mesh (Standard U.S. Mesh) (1.9 mm to 250μ).

Feed mixtures which can be used in the separation process of the invention include complex mixtures of naphthalene and substituted paraffins, substituted benzenes and substituted indans derived from petroleum or coal tar in narrow boiling point fractions in the range between 200° C. and 250° C. In Table 1 following is an analysis of a typical coal tar distillate fraction with boiling point range of 208°–236° C. which may be separated by the present invention. The particular sample contained about 60% naphthalene and no known methylnaphthalenes. A question mark (?) follows a component which was not identified with certainty. Several components were not identified and are listed as unknown. The sample contained various paraffins, substituted monocyclic aromatics, including indans, and naphthalene.

TABLE 1

| GC-MS Analysis of Coal Tar Distillate Feed | | |
|---|---|---|
| Peak # | Retention Time Minutes | Compound Identification |
| 1 | 4.01 | Dodecane |
| 2 | 4.11 | Trimethyldodecane |
| 3 | 4.18 | Unknown |
| 4 | 4.26 | Tridecane |
| 5 | 4.72 | Unknown |
| 6 | 4.80 | Unknown |
| 7 | 4.89 | Diethylmethylbenzene |
| 8 | 4.97 | Diethylmethylbenzene |
| 9 | 5.03 | Unknown |
| 10 | 5.10 | Methylpropylbenzene |
| 11 | 5.16 | Unknown |
| 12 | 5.24 | Unknown |
| 13 | 5.37 | Diethylmethylbenzene |
| 14 | 5.43 | Trimethylethylbenzene |
| 15 | 5.60 | Dimethylpropylbenzene |
| 16 | 5.72 | Trimethylethylbenzene |
| 17 | 5.79 | Dimethyldiethylbenzene |
| 18 | 5.87 | Dimethyldiethylbenzene |
| 19 | 5.95 | Dimethylpropylbenzene |
| 20 | 6.04 | Methyltetralin (?) |
| 21 | 6.14 | Ethylindan (?) |
| 22 | 6.39 | Dimethylindan |
| 23 | 6.62 | Dimethylindan |
| 24 | 6.73 | Trimethylethylbenzene |
| 25 | 6.94 | Dimethylindan |
| 26 | 7.86 | Naphthalene |
| 27 | 10.90 | Biphenyl |

The present process is suitable for feeds containing 60 wt. % or greater naphthalene in the feed mixture, but economic benefit may also be derived from the process when the feed mixture contains minor amounts of naphthalene.

In the preferred isothermal, isobaric, liquid-phase operation of the process of the invention, we have found that desorbent materials comprising aromatic hydrocarbons, selected to differ in boiling point by at least about 5° C. from the boiling point range of the feedstock so that the desorbent may be recovered for reuse, will result in selectivity for the extracted product when used with the aforesaid adsorbent. Suitable aromatic hydrocarbons are 1,2,3-trimethylbenzene, mesitylene, toluene, p-xylene, benzene and m-xylene. Benzene and 1,2,3-TMB are particularly preferred.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 20° to about 200° C. and a pressure sufficient to maintain liquid phase, ranging from about atmospheric to about 500 psig. Desorption conditions will include the same range of temperatures and pressures as used for adsorption conditions.

At least a portion of the extract stream, and preferably at least a portion of the raffinate stream, from the separation process, are passed to separation means, typically fractionators or evaporators, where at least a portion of the desorbent material is separated to produce an extract product and a raffinate product, respectively.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of the feed mixture is injected for a duration of several minutes. Desorbent flow is resumed, and naphthalene extract and raffinate components are separately eluted as in a liquid-solid chromatographic operation. The effluent can be analyzed on stream or alternatively, effluent samples can be collected periodically and later analyzed separately by analytical equipment and traces of the envelopes of corresponding component peaks developed.

From information derived from the test, adsorbent performance can be rated in terms of void volume, retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component (assumed to be void volume) or some other known reference point. It is expressed in terms of the volume in cubic centimeters of desorbent pumped during the time interval represented by the distance between the peak envelopes. Selectivity, ($\beta$), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume (cc) of desorbent pumped during this time interval.

The following examples are presented to illustrate the process of this invention. The examples are not intended to unduly restrict the scope of the claims.

EXAMPLE I

A pulse test as described above was performed to evaluate the process of the present invention for separating naphthalene from a mixture of hydrocarbons in the boiling point range of 208° to 236° C., derived from coal tar distillation, and having the composition set forth in Table 1 above. The adsorbent was lithium exchanged X zeolite; the desorbent was 1,2,3-trimethylbenzene (hemimellitene). The temperature of the column was maintained at 180° C. during the test. A 2 cc pulse of 40 wt. % of the above naphthalene and 20 wt. % of $n$—$C_{14}$ as tracer with 40 wt. % of desorbent was injected into the column. The results are as shown in the following Table 2 under the headings Gross Retention Volume (GRV), Net Retention Volumn (NRV) and Selectivity, ($\beta$). The results are also shown in FIG. 1. Naphthalene was well separated from all other components in the feed mixture. Because of the difficulty in analyzing for specific components in the complex feed mixture and since all remaining feed components were relatively non-adsorbed and eluted near the void volume as raffinate components, groups of unidentified raffinate components were combined and plotted as Unknown Group A, Unknown Group B, etc.

TABLE 2

| Component | GRV | NRV | Selectivity $\beta$ |
|---|---|---|---|
| RT,-$C_{14}$ | 37.2 | 0.0 | x |
| Unknown Group A | 41.6 | 4.4 | 8.79 |
| Unknown Group B | 42.0 | 4.8 | 8.01 |
| Unknown Group C | 44.3 | 7.1 | 5.40 |
| Unknown Group D | 45.6 | 8.3 | 4.60 |
| Naphthalene | 75.6 | 38.4 | 1.00 (Ref.) |

EXAMPLE II

Two further pulse tests as described above were performed to evaluate other aromatic desorbents. In these, the same naphthalene feed was diluted and contacted in the column with the same adsorbent as in Example I at a temperature of 180° C. and 200° C., respectively. In the first pulse, the pulse 1 sample was a 40:40:20 (wt. %) naphthalene: n-hexane: $n$—$C_{14}$ mixture and the desorbent was m-xylene; in the second, the desorbent was benzene and the sample was a 40:40:20 (wt. %) mixture of naphthalene: 1,2,3-trimethylbenzene: n—$C_{14}$ and the desorbent was benzene. All other conditions were the same. The results of the first in which naphthalene was separated from all components except for two minor unknown species (labelled Groups F and G) are set forth in the following Table 3 under the same headings.

TABLE 3

| Component | GRV | NRV | Selectivity $\beta$ |
|---|---|---|---|
| $n$-$C_{14}$ | 43.0 | 0.0 | x |
| n-hexane | 44.5 | 1.5 | 28.46 |

TABLE 3-continued

| Component | GRV | NRV | Selectivity β |
|---|---|---|---|
| Unknown Group A | 46.9 | 3.9 | 10.76 |
| Unknown Group B | 49.7 | 6.7 | 6.26 |
| Unknown Group C | 49.8 | 6.7 | 6.19 |
| Unknown Group D | 50.3 | 7.3 | 5.71 |
| Unknown Group E | 52.9 | 9.9 | 4.20 |
| Naphthalene | 84.7 | 41.7 | 1.00 (Ref.) |
| Unknown Group F | 92.4 | 49.3 | 0.84 |
| Unknown Group G | 92.1 | 49.1 | 0.85 |

The results of the second pulse test, in which naphthalene was separated from all other feed components, are set forth in the following Table 4.

TABLE 4

| Component | GRV | NRV | Selectivity β |
|---|---|---|---|
| n-C14 | 39.1 | 0.0 | ∞ |
| Unknown Group A | 39.1 | 0.0 | — |
| Unknown Group B | 39.0 | −0.1 | — |
| Unknown Group C | 42.7 | 3.6 | 7.57 |
| Unknown Group D | 44.1 | 5.0 | 5.53 |
| Unknown Group E | 45.4 | 6.3 | 4.39 |
| Unknown Group F | 46.6 | 7.5 | 3.65 |
| Unknown Group G | 50.1 | 11.0 | 2.40 |
| Naphthalene | 66.5 | 27.4 | 1.00 (Ref.) |

What is claimed:

1. A process for separating naphthalene from a hydrocarbon mixture comprising naphthalene, substituted monocyclic aromatic hydrocarbons and paraffins boiling in the range from 200° to 250° C., said process comprising contacting said mixture at adsorption conditions with an adsorbent consisting essentially of an X zeolite exchanged with lithium cations at exchangeable sites thereby selectively adsorbing said naphthalene thereon, removing said monocyclic aromatic hydrocarbons and paraffins from contact with said adsorbent and desorbing said naphthalene with a liquid aromatic desorbent having a boiling point at least 5° C. higher or lower than the boiling point range of said hydrocarbon mixture.

2. The process of claim 1 wherein said hydrocarbon mixture comprises naphthalenes, substituted benzenes, substituted indans and paraffins.

3. The process of claim 1 wherein said adsorption and desorption conditions include a temperatur within the range of from about 20° C. to about 220° C. and a pressure sufficient to maintain liquid phase.

4. The process of claim 1 wherein said desorbent is selected from the group consisting of 1,2,3-trimethylbenzene, 1,3,5-trimethylbenzene, toluene, p-xylene, m-xylene and benzene.

5. The process of claim 1 wherein said desorbent is 1,2,3-trimethylbenzene.

* * * * *